United States Patent [19]

Cherpeck

[11] Patent Number: 5,296,003
[45] Date of Patent: Mar. 22, 1994

[54] POLYESTERS OF POLY(OXYALKYLENE) HYDROXYAROMATIC ETHERS

[75] Inventor: Richard E. Cherpeck, Cotati, Calif.

[73] Assignee: Chevron Research and Technology Company, San Francisco, Calif.

[21] Appl. No.: 28,024

[22] Filed: Mar. 8, 1993

[51] Int. Cl.$^5$ .................. C10L 1/18; C07C 69/76; C07C 69/34; C07C 69/66

[52] U.S. Cl. .................. 44/389; 44/398; 554/229; 560/66; 560/85; 560/105; 560/106; 560/146; 560/185; 560/193

[58] Field of Search ............. 554/229; 560/66, 85, 560/105, 106, 146, 185, 193; 44/389, 398

[56] References Cited

U.S. PATENT DOCUMENTS

| | | | |
|---|---|---|---|
| 3,810,929 | 5/1974 | Song | 560/85 |
| 3,846,089 | 11/1974 | Machleder et al. | 44/398 |
| 3,849,085 | 11/1974 | Kreuz et al. | 44/78 |
| 3,912,771 | 10/1975 | Kuhn et al. | 44/398 |
| 4,010,007 | 3/1977 | Bollinger et al. | 44/398 |
| 4,040,798 | 8/1977 | Kuhn et al. | 44/398 |
| 4,072,474 | 2/1978 | Kuhn et al. | 44/398 |
| 4,134,846 | 1/1979 | Machleder et al. | 252/51.5 |
| 4,191,537 | 3/1980 | Lewis et al. | 44/71 |
| 4,261,912 | 4/1981 | Tracy | 560/85 |
| 4,395,568 | 7/1983 | Molnar et al. | 560/85 |
| 4,952,732 | 8/1990 | Speranza et al. | 564/390 |

FOREIGN PATENT DOCUMENTS

687696  6/1964  Canada.

*Primary Examiner*—Jerry D. Johnson
*Attorney, Agent, or Firm*—C. J. Caroli

[57] ABSTRACT

Poly(oxyalkylene) hydroxyaromatic ethers having the formula:

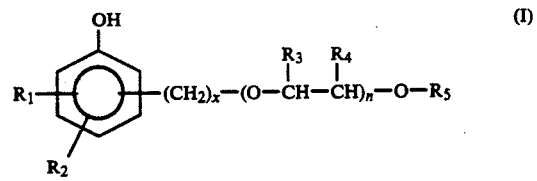

or a fuel-soluble salt thereof; where n is an integer from 5 to 100; x is an integer from 0 to 10; $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; $R_5$ is an acyl group of the formula:

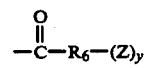

wherein y is 1, 2 or 3; $R_6$ is a divalent hydrocarbyl radical, when y is 1, a trivalent hydrocarbyl radical, when y is 2, or tetravalent hydrocarbyl radical, when y is 3, said hydrocarbyl radicals having 1 to about 20 carbon atoms; and each Z is independently selected from the group consisting of:

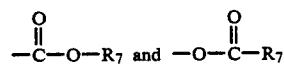

where each $R_7$ is independently alkyl having 1 to 30 carbon atoms, phenyl, aralkyl having 7 to 36 carbon atoms or alkaryl having 7 to 36 carbon atoms.

The poly(oxyalkylene) hydroxyaromatic ethers of formula I are useful as fuel additives for the prevention and control of engine deposits.

24 Claims, No Drawings

POLYESTERS OF POLY(OXYALKYLENE) HYDROXYAROMATIC ETHERS

BACKGROUND OF THE INVENTION

1. Field of the Invention

This invention relates to novel hydroxyaromatic compounds. More particularly, this invention relates to novel poly(oxyalkylene) hydroxyaromatic ethers and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amount of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at o least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, Water repellent agents, paint adhesion promotors, and also as intermediates for preparing surfactants, and polyols finding use in the manufacture of polyurethane foam.

It has now been discovered that certain hydroxyaromatic ethers having a poly(oxyalkylene) "tail" provide excellent control of engine deposits, especially intake valve deposits, when employed as fuel additives in fuel compositions.

SUMMARY OF THE INVENTION

The present invention provides novel poly(oxyalkylene) hydroxyaromatic ethers which are useful as fuel additives for the prevention and control of engine deposits, particularly intake valve deposits.

The poly(oxyalkylene) hydroxyaromatic ethers of the present invention have the formula:

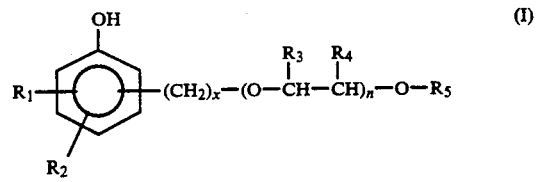

or a fuel-soluble salt thereof; wherein n is an integer from 5 to 100; x is an integer from 0 to 10; $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; and $R_5$ is an acyl group of the formula:

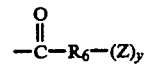

wherein y is 1, 2 or 3; $R_6$ is a divalent hydrocarbyl radical, when y is 1, a trivalent hydrocarbyl radical, when y is 2, or tetravalent hydrocarbyl radical, when y is 3, said hydrocarbyl radicals having 1 to about 20 carbon atoms; and further wherein each Z is independently selected from the group consisting of:

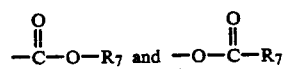

wherein each $R_7$ is independently alkyl having 1 to 30 carbon atoms, phenyl, aralkyl having 7 to 36 carbon atoms or alkaryl having 7 to 36 carbon atoms.

The present invention further provides a fuel composition comprising a major amount of hydrocarbons boiling in the gasoline or diesel range and an effective deposit-controlling amount of a hydroxyaromatic poly(oxyalkylene) ether of the present invention.

The present invention additionally provides a fuel concentrate comprising an inert stable oleophilic organic solvent boiling in the range of from about 150° F. to 400° F. and from about 10 to 70 weight percent of a hydroxyaromatic poly(oxyalkylene) ether of the present invention.

Among other factors, the present invention is based on the surprising discovery that certain poly(oxyalkylene) hydroxyaromatic ethers, when employed as fuel additives in fuel compositions, provide excellent control of engine deposits, especially on intake valves.

DETAILED DESCRIPTION OF THE INVENTION

The fuel additives provided by the present invention have the general formula:

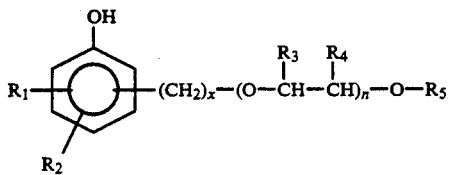

(I)

or a fuel-soluble salt thereof; wherein $R_1$, $R_2$, $R_3$, $R_4$, $R_5$, n and x are as defined hereinabove.

Preferably, $R_1$ is hydrogen, hydroxy, or lower alkyl having 1 to 4 carbon atoms. More preferably, $R_1$ is hydrogen or s hydroxy. Most preferably, $R_1$ is hydrogen.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably an acyl group of the formula:

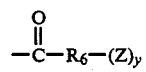

wherein y is 1 or 2; and $R_6$ and Z are as defined above. Most preferably, y is 1.

More preferably, $R_5$ is an acyl group having the formula:

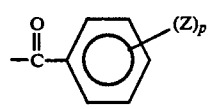

wherein Z is as defined above; and p is 1 or 2; or an acyl group having the formula:

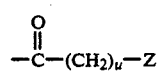

wherein Z is as defined above; and u is an integer from 1 to 10; or an acyl group having the formula:

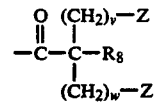

wherein Z is as defined above; $R_8$ is hydrogen or lower alkyl having 1 to about 6 carbon atoms; v is an integer from 1 to 6; and w is an integer from 1 to 6. Preferably, $R_8$ is hydrogen or methyl.

$R_7$ is preferably alkyl having 1 to about 10 carbon atoms. More preferably, $R_7$ is alkyl having 1 to 6 carbon atoms.

Preferably, n is an integer from 5 to 50. More preferably, n is an integer from 10 to 30. Preferably, x is an integer from 0 to 2. More preferably, x is 0.

A preferred group of poly(oxyalkylene) hydroxyaromatic ethers are those of formula I wherein n is 5 to 50; x is 0, 1, or 2; $R_1$ is hydrogen, hydroxy, or lower alkyl having 1 to 4 carbon atoms; $R_2$ is hydrogen; one of $R_3$ and $R_4$ is hydrogen and the other is methyl or ethyl; and $R_5$ is an acyl group having the formula:

wherein $R_9$ is alkyl having 1 to about 10 carbon atoms.

Another preferred group of poly(oxyalkylene) hydroxyaromatic ethers are those of formula I wherein n is 5 to 50; x is 0, 1, or 2; $R_1$ is hydrogen, hydroxy, or lower alkyl having 1 to 4 carbon atoms; $R_2$ is hydrogen; one of $R_3$ and $R_4$ is hydrogen and the other is methyl or ethyl; and $R_5$ is an acyl group having the formula:

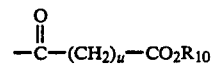

wherein $R_{10}$ is alkyl having 1 to about 10 carbon atoms and u is an integer from 1 to 10.

Another preferred group of poly(oxyalkylene) hydroxyaromatic ethers are those of formula I wherein n is 5 to 50; x is 0, 1, or 2; $R_1$ is hydrogen or hydroxy; $R_2$ is hydrogen; one of $R_3$ and $R_4$ is hydrogen and the other is methyl or ethyl; and $R_5$ is an acyl group having the formula:

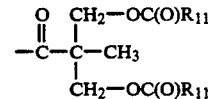

wherein $R_{11}$ is alkyl having 1 to about 10 carbon atoms.

A particularly preferred group of poly(oxyalkylene) hydroxyaromatic ethers are those having the formula:

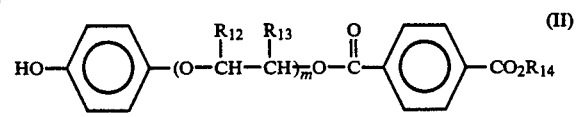

(II)

wherein one of $R_{12}$ and $R_{13}$ is methyl or ethyl and the other is hydrogen; $R_{14}$ is lower alkyl having 1 to 6 carbon atoms; and m is an integer from 10 to 30.

The poly(oxyalkylene) hydroxyaromatic ethers of the present invention will generally have a sufficient molecular weight so as to be non-volatile at normal engine intake valve operating temperatures (about 200°-250° C.). Typically, the molecular weight of the poly(oxyalkylene) hydroxyaromatic ethers of this invention will range from about 600 to about 10,000, preferably from 1,000 to 3,000.

Generally, the poly(oxyalkylene) hydroxyaromatic ethers of this invention will contain an average of about 5 to about 100 oxyalkylene units; preferably, 5 to 50 oxyalkylene units; more preferably, 10 to 30 oxyalkylene units.

Fuel-soluble salts of the poly(oxyalkylene) hydroxyaromatic ethers of the present invention are also contemplated to be useful for preventing or controlling deposits. Such salts include alkali metal, alkaline earth metal, ammonium, substituted ammonium and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Definitions

As used herein the following terms have the following meanings unless expressly stated to the contrary.

The term "hydrocarbyl" refers to an organic radical composed primarily of carbon and hydrogen which may be aliphatic, alicyclic, aromatic or combinations thereof (e.g. aralkyl or alkaryl). Such hydrocarbyl groups are generally relatively free of aliphatic unsaturation, i.e. olefinic or acetylenic unsaturation.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —OR$_a$ wherein R$_a$ is lower alkyl. Typical lower alkoxy groups include methoxy, ethoxy, and the like.

The term "alkaryl" refers to the group:

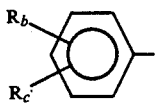

wherein R$_b$ and R$_c$ are each independently hydrogen or an alkyl group, with the proviso that both R$_b$ and R$_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which R$_b$ is alkyl and R$_c$ is hydrogen.

The term "aralkyl" refers to the group:

wherein R$_d$ and R$_e$ are each independently hydrogen or an alkyl group; and R$_f$ is an alkylene group. Typical alkaryl groups include, for example, benzyl, methylbenzyl, dimethylbenzyl, phenethyl, and the like.

The term "oxyalkylene unit" refers to an ether moiety having the general formula:

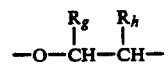

wherein R$_g$ and R$_h$ are each independently hydrogen or lower alkyl groups.

The term "poly(oxyalkylene)" refers to a polymer or oligomer having the general formula:

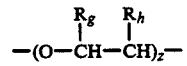

wherein R$_g$ and R$_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) hydroxyaromatic ethers of this invention may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(oxyalkylene) hydroxyaromatic ethers of the present invention may be prepared from a hydroxyaromatic compound having the formula:

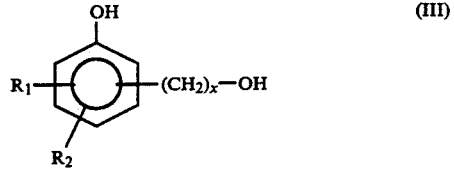

wherein R$_1$, R$_2$, and x are as defined above.

The hydroxyaromatic compounds of formula III are either known compounds or can be prepared from known compounds by conventional procedures. Suitable hydroxyaromatic compounds for use as starting materials in this invention include catechol, resorcinol, hydroquinone, 1,2,3-trihydroxybenzene (pyrogallol), 1,2,4-trihydroxybenzene (hydroquinol), 1,3,5-trihydroxybenzene (phloroglucinol), 1,4-dihydroxy-2-methylbenzene, 1,3-dihydroxy-5-methylbenzene, 2-t-butyl- 1,4-dihydroxybenzene, 2,6-di-t-butyl-1,4-dihydroxybenzene, 1,4-dihydroxy-2-methoxybenzene, 1,3-dihydroxy-5-methoxybenzene, 4-hydroxybenzyl alcohol, 4-hydroxyphenethyl alcohol and the like.

In a preferred method of synthesizing the poly(oxyalkylene) hydroxyaromatic ethers of the present invention, a hydroxyaromatic compound of formula III is first selectively protected to provide a compound having the formula:

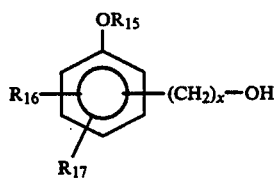
(IV)

wherein $R_{15}$ is a suitable hydroxyl protecting group, such as benzyl, tert-butyldimethylsilyl, methoxymethyl, and the like; $R_{16}$ and $R_{17}$ are each independently hydrogen, lower alkyl, lower alkoxy, or the group —$OR_{18}$, wherein $R_{18}$ is a suitable hydroxyl protecting group, such as benzyl, tert-butyldimethylsilyl, methoxymethyl, and the like. Preferably, $R_{15}$ and $R_{18}$ are benzyl; except in the case where x is 1, then $R_{15}$ and $R_{18}$ are preferably a tert-butyl-dimethylsilyl group.

Selective protection of III may be accomplished using conventional procedures. The choice of a suitable protecting group for a particular hydroxyaromatic compound will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein. Alternatively, the protected derivatives IV can be prepared from known starting materials other than the hydroxyaromatic compounds of formula III by conventional procedures. In some cases, the protected derivatives IV are commercially available, e.g. 4-benzyloxyphenol is commercially available from Aldrich Chemical Co., Milwaukee, Wis. 53233.

The protected hydroxyaromatic compound of formula IV is then deprotonated with a suitable base to provide a metal salt having the formula:

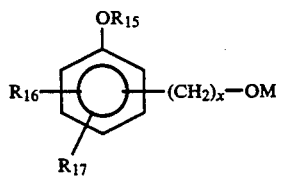
(V)

wherein $R_{15}$, $R_{16}$, $R_{17}$ and x are as defined above; and M is a metal cation, such as lithium, sodium or potassium.

Generally, this deprotonation reaction will be effected by contacting IV with a strong base, such as sodium hydride, potassium hydride, sodium amide and the like, in an inert solvent, such as toluene, xylene and the like, under substantially anhydrous conditions at a temperature in the range from about $-10°$ C. to about $120°$ C. for about 0.25 to about 3 hours.

Metal salt V is generally not isolated, but is reacted in situ with about 5 to about 100 molar equivalents of an alkylene oxide (an epoxide) having the formula

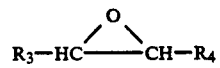
(VI)

wherein $R_3$ and $R_4$ are as defined above, to provide, after neutralization, a poly(oxyalkylene) polymer or oligomer having the formula:

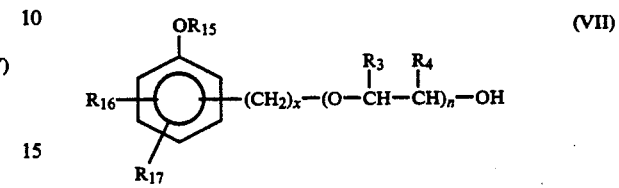
(VII)

wherein $R_3$, $R_4$, $R_{15}$, $R_{16}$, $R_{17}$, n and x are as defined above.

Typically, this polymerization reaction is conducted in a substantially anhydrous inert solvent at a temperature of about 30° C. to about 150° C. for about 2 to about 120 hours. Suitable solvents for this reaction, include toluene, xylene and the like. The reaction will generally be conducted at a pressure sufficient to contain the reactants and the solvent, preferably at atmospheric or ambient pressure. More detailed reaction conditions for preparing poly(oxyalkylene) compounds may be found in U.S. Pat. Nos. 2,782,240 and 2,841,479, which are incorporated herein by reference.

The amount of alkylene oxide employed in this reaction will depend on the number of oxyalkylene units desired in the product. Typically, the molar ratio of alkylene oxide VI to metal salt V will range from about 5:1 to about 100:1; preferably, from 5:1 to 50:1, more preferably from 10:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g. propylene oxide, in which case the product is a homopolymer, e.g. a poly(oxypropylene). However, copolymers are equally satisfactory and random copolymers are readily prepared by contacting the metal salt V with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt V with first one alkylene oxide, then others in any order, or repetitively, under polymerization conditions.

Poly(oxyalkylene) polymers of formula VII may also be prepared by living or immortal polymerization as described by S. Inoue and T. Aida in *Encyclopedia of Polymer Science and Engineering*, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

Acylation of the poly(oxyalkylene) polymer of formula VII with an acyl halide having the formula:

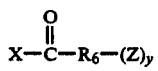

wherein $R_6$, y and Z are as defined above; and X is a halogen, preferably chloride or bromide, then provides an intermediate having the formula:

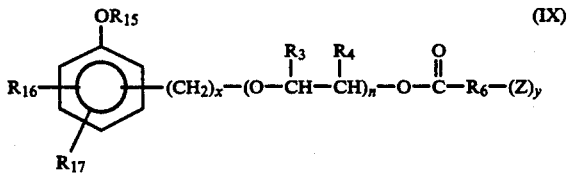

wherein $R_3$, $R_4$, $R_6$, $R_{15}$, $R_{16}$, $R_{17}$, n, x, y and Z are as defined above.

Generally, this acylation reaction will be conducted by contacting intermediate VII with about 0.95 to about 1.2 molar equivalents of a suitable acyl halide of formula VIII. This reaction is typically conducted in an inert solvent, such as toluene, dichloromethane, diethyl ether and the like, at a temperature in the range of about 25° C. to about 150° C., and is generally complete in about 0.5 to about 48 hours. The reaction is preferably conducted in the presence of a sufficient amount of an amine capable of neutralizing the acid generated during the reaction, such as triethylamine, di(isopropyl)ethylamine, pyridine or 4-dimethylaminopyridine.

The acyl halide VIII will generally be derived from a corresponding carboxylic acid having the formula:

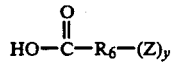

wherein $R_6$, y and Z are as defined above, by contacting X with an inorganic acid halide, such as thionyl chloride, phosphorous trichloride, phosphorous tribromide, or phosphorous pentachloride; or alternatively, with oxalyl chloride. Generally, this reaction will be conducted using about 1 to 5 molar equivalents of the inorganic acid halide or oxalyl chloride, either neat or in an inert solvent, such as diethyl ether, at a temperature in the range of about 20° C. to about 80° C. for about 1 to about 48 hours. A catalyst, such as N,N-dimethylformamide, may also be used in this reaction.

The carboxylic acids of formula X employed in the present invention preferably contain 1 to 3 ester moieties, i.e. ester functional groups having the formula —C(O)OR$_7$ or —OC(O)R$_7$, wherein R$_7$ is as defined above. The ester moieties of X are typically separated from the carboxylic acid functional group by a hydrocarbyl radical, $R_6$, having 1 to about 20 carbon atoms, preferably 2 to 10 carbon atoms, more preferably 4 to 6 carbon atoms. When carboxylic acid X contains one ester moiety (i.e. when y=1), $R_6$ is a divalent hydrocarbyl radical. When carboxylic acid X contains two ester moieties (i.e. when y=2), $R_6$ is a trivalent hydrocarbyl radical; and when carboxylic acid X contains three ester moieties (i.e. when y=3), $R_6$ is a tetravalent hydrocarbyl radical. The hydrocarbyl radical $R_6$ may be any hydrocarbyl group having 1 to about 20 carbon atoms, including straight- or branched-chain aliphatic or alicyclic hydrocarbyl groups, aromatic hydrocarbyl groups, or combinations thereof. The carboxylic acids of formula X are either known compounds or can be prepared from known compounds by conventional procedures.

A preferred group of carboxylic acids for use in the present invention are those having the formula:

wherein $R_9$ is alkyl having 1 to about 10 carbon atoms and p is 1 or 2.

Suitable carboxylic acids of formula XI include the mono-alkyl esters of phthalic acid, isophthalic acid and terephthalic acid; and the dialkyl esters of 1,2,3-benzenetricarboxylic acid (hemimellitic acid), 1,2,4-benzenetricarboxylic acid (trimellitic acid), and 1,3,5-benzenetricarboxylic acid (trimesic acid). Representative examples of such compounds include, mono-methyl phthalate, mono-methyl isophthalate, mono-methyl terephthalate, mono-ethyl terephthalate, mono-n-butyl isophthalate, mono-iso-octyl terephthalate, dimethyl 1,2,3-benzenetricarboxylate, dimethyl 1,3,5-benzenetricarboxylate, diethyl 1,2,4-benzenetricarboxylate and the like. The mono-alkyl esters of isophthalic acid and terephthalic acid are particularly preferred for use in the present invention, especially mono-alkyl esters of terephthalic acid. The carboxylic acids of formula XI are commercially available or may be prepared by known procedures, e.g. mono-methyl terephthalate is commercially available from Aldrich Chemical Co., Milwaukee, Wis. 53233.

Another preferred group of carboxylic acids for use in the present invention are those having the formula:

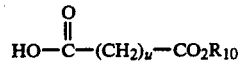

wherein $R_{10}$ is alkyl having 1 to about 10 carbon atoms and u is an integer from 1 to 10.

Suitable carboxylic acids of formula XII include the mono-alkyl esters of malonic acid, succinic acid, glutaric acid, adipic acid, pimelic acid, suberic acid, azelaic acid and sebacic acid. Representative examples of such compounds include malonic acid mono-methyl ester, succinic acid mono-ethyl ester, adipic acid monomethyl ester, pimelic acid mono-n-butyl ester and the like. The mono-alkyl esters of these dicarboxylic acids are commercially available or may be prepared by known procedures, e.g. adipic acid mono-methyl ester and mono-ethyl ester are commercially available from Aldrich Chemical Co., Milwaukee, Wis. 53233.

Another preferred group of carboxylic acids finding use in the present invention are those having the formula:

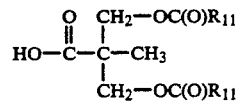

wherein $R_{11}$ is alkyl having 1 to about 10 carbon atoms.

The carboxylic acids of formula XIII are diester derivatives of 2,2-bis(hydroxymethyl)propionic acid. The ester groups of XIII will generally be derived from aliphatic carboxylic acids having 1 to about 10 carbon atoms. Typical esters include, for example, acetate, propionate, butyrate, valerate, hexanoate, octanoate, decanoate and the like. The carboxylic acids of formula XIII can be readily prepared by acylation of 2,2-bis(hydroxymethyl)propionic acid with a suitable acyl halide or anhydride, such as decanoyl chloride, using conventional procedures well known in the art.

Other carboxylic acids of formula X suitable for use in preparing the poly(oxyalkylene) hydroxyaromatic ethers of the present invention include, but are not limited to, acylated derivatives of mono- and dihydroxybenzoic acids, including acylated derivatives of 2-hydroxybenzoic acid, 3-hydroxybenzoic acid, 4-hydroxybenzoic acid, 3,4-dihydroxybenzoic acid, 3,5-dihydroxybenzoic acid and the like, such as 4-acetoxybenzoic acid; acylated derivatives of hydroxy-aliphatic carboxylic acids, including acylated derivatives of glycolic acid, lactic acid, 3-hydroxybutyric acid, 4-hydroxybutyric acid, 2-hydroxyvaleric acid and the like, such as 2-decanoyloxyacetic acid; and diesters of tricarballylic acid (1,2,3-propanetricarboxylic acid), such as dimethyl tricarballylate, dioctyl tricarballylate and the like.

As discussed above, intermediate IX is generally prepared by acylating VII with acyl halide VIII. However, IX may also be prepared by directly esterifying VII with a carboxylic acid of formula X using conventional esterification reaction conditions. Typically, this reaction is conducted by contacting VII with about 0.25 to about 1.5 molar equivalents of a carboxylic acid formula X in the presence of an acidic catalyst at a temperature in the range of 70° C. to about 160° C. for about 0.5 to about 48 hours. Suitable acid catalysts for this reaction include p-toluenesulfonic acid, methanesulfonic acid and the like. The reaction may be conducted in the presence or absence of an inert solvent, such as benzene, toluene and the like. The water generated by this reaction is preferably removed during the course of the reaction by, for example, azeotropic distillation with an inert solvent, such as toluene.

Additional methods for preparing esters from alcohols and carboxylic acids, and suitable reaction conditions for such reactions, can also be found, for example, in I. T. Harrison and S. Harrison, *Compendium of Organic Synthetic Methods*, Vol. 1, pp. 273-276 and 280-283, Wiley-Interscience, New York (1971) and references cited therein.

The poly(oxyalkylene) hydroxyaromatic ethers of formula I can be prepared from intermediate IX by deprotection of the aromatic hydroxyl group(s) present in IX using conventional procedures. Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction will be conducted in an inert solvent, preferably a mixture of ethyl acetate and acetic acid, at a temperature of from about 0° C. to about 40° C. for about 1 to about 24 hours.

Fuel Compositions

The poly(oxyalkylene) hydroxyaromatic ethers of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the poly(oxyalkylene) hydroxyaromatic ethers of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) hydroxyaromatic ethers of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) hydroxyaromatic ethers of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, synthetic polyoxyalkylene-derived oils, such as those described, for example, in U.S. Pat. No. 4,191,537 to Lewis, or a polyester, such as those described, for example, in U.S. Pat. Nos. 3,756,793 and 5,004,478 to Robinson and Vogel et al., respectively, and in European Patent Application Nos. 356,726 and 382,159, published Mar. 7, 1990 and Aug. 16, 1990, respectively.

These carrier fluids are believed to act as a carrier for the fuel additives of the present invention and to assist in removing and retarding deposits. The carrier fluid may also exhibit synergistic deposit control properties when used in combination with the poly(oxyalkylene) hydroxyaromatic ethers of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and should not be interpreted as limitations upon the scope of the invention.

Example 1

Preparation of α-(4-Benzyloxyphenyl)-ω-hydroxypoly(oxybutylene)

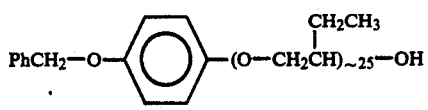

To a flask equipped with a magnetic stirrer, thermometer, addition funnel, reflux condenser and nitrogen inlet was added 6.88 grams of a 35 wt % dispersion of potassium hydride in mineral oil. Forty grams of 4-benzyloxyphenol dissolved in 500 mL of anhydrous toluene was added dropwise and the resulting mixture was stirred at room temperature for ten minutes. The temperature of the reaction mixture, a thick white suspension, was raised to 90° C. and 430.8 mL of 1,2-epoxybutane was added dropwise. The reaction mixture was refluxed until the pot temperature reached 110° C. (approximately 48 hours) at which time the reaction mixture was a light brown clear solution. The reaction was cooled to room temperature, quenched with 50 mL of methanol and diluted with 1 liter of diethyl ether. The resulting mixture was washed with saturated aqueous ammonium chloride, followed by water and saturated aqueous sodium chloride. The organic layer was dried over anhydrous magnesium sulfate, filtered and the solvents removed in vacuo to yield 383.3 grams of the desired product as a yellow oil.

Example 2

Preparation of Methyl Adipoyl Chloride

To a flask equipped with a magnetic stirrer and drying tube was added 7.4 mL of mono-methyl adipate and 100 mL of anhydrous diethyl ether and then 21.8 mL of oxalyl chloride. The resulting mixture was stirred at room temperature for 16 hours and then the solvent was removed in vacuo to yield 8.0 grams of the desired acid chloride.

Example 3

Preparation of α-(4-Benzyloxyphenyl)-ω-(mono-methyl adipoyloxy)poly(oxybutylene)

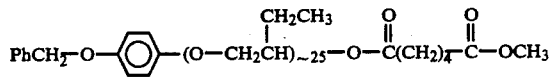

Methyl adipoyl chloride (3.57 grams) from Example 2 was combined with 42.48 grams of α-(4-benzyloxyphenyl)-ω-hydroxypoly(oxybutylene) from Example 1 having an average of 25 oxybutylene units and 200 mL of anhydrous toluene. Triethylamine (3.1 mL) and 4-dimethylaminopyridine (1.22 grams) were then added and the resulting mixture was heated to reflux under nitrogen for 16 hours. The reaction was then cooled to room temperature and diluted with 400 mL of hexane. The organic layer was washed twice with water, twice with saturated aqueous sodium bicarbonate solution and once with saturated aqueous sodium chloride. The organic layer was then dried over anhydrous magnesium sulfate, filtered and the solvents removed in vacuo to yield 40.23 grams of the desired ester.

Example 4

Preparation of α-(4-Hydroxyphenyl)-ω-(mono-methyl adipoyloxy)poly(oxybutylene)

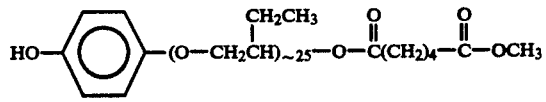

A solution of the ester from Example 3 (40.23 grams) in 100 mL of ethyl acetate and 100 mL of acetic acid containing 5.0 grams of 10% palladium on charcoal was hydrogenolyzed at 35–40 psi for 16 hours on a Parr low-pressure hydrogenator. Filtration of the catalyst and removal of solvent in vacuo followed by azeotropic removal of residual acetic acid with toluene under vacuum yielded 36.3 grams of the desired product as a colorless oil. The product had an average of 25 oxybutylene units. IR (neat) 1742 cm$^{-1}$; $^1$H NMR (CDCl$_3$)δ 6.7 (s, 4H), 4.7–4.8 (m, 1H), 3.0–4.0 (m, 78H), 2.2(t, 4H), 0.6–1.7(m, 129H).

Example 5

Preparation of Methyl Terephthaloyl Chloride

To a flask equipped with a magnetic stirrer, reflux condenser and drying tube was added 9.0 grams of mono-methyl terephthalate and 36 mL of thionyl chloride. The resulting mixture was heated at reflux for 16 hours and then cooled to room temperature. The excess thionyl chloride was removed in vacuo to yield the desired acid chloride as a white solid.

Example 6

Preparation of α-(4-Benzyloxyphenyl)-ω-(mono-methyl terephthaloyloxy)poly(oxybutylene)

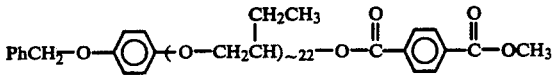

Methyl terephthaloyl chloride (5.0 grams) from Example 5 was combined with 40.75 grams of α-(4-benzyloxyphenyl)-ω-hydroxypoly(oxybutylene) containing an average of 22 oxybutylene units (prepared essentially as described in Example 1) and 200 mL of anhydrous toluene. Triethylamine (3.9 mL) and 4-dimethylaminopyridine (1.5 grams) were then added and the resulting mixture was heated to reflux under nitrogen for 16 hours. The reaction was then cooled to room temperature and diluted with 400 mL of hexane. The organic layer was washed twice with water, twice with saturated aqueous sodium bicarbonate and once with saturated aqueous sodium chloride. The organic layer was then dried over anhydrous magnesium sulfate, filtered and the solvents removed in vacuo to yield 48.0 grams of the desired ester as a yellow oil.

Example 7

Preparation of α-(4-Hydroxyphenyl)-ω-(mono-methyl terephthaloyloxy)poly(oxybutylene)

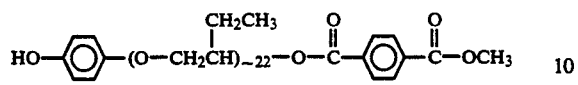

A solution of the ester from Example 6 (48.0 grams) in 100 mL of ethyl acetate and 100 mL of acetic acid containing 6.0 grams of 10% palladium on charcoal was hydrogenolyzed at 35-40 psi for 16 hours on a Parr low-pressure hydrogenator. Filtration of the catalyst and removal of solvent in vacuo followed by azeotropic removal of residual acetic acid with toluene under vacuum yielded 34.0 grams of the desired product as a brown oil. The product had an average of 22 oxybutylene units. IR (neat) 1729 cm$^{-1}$; $^1$H NMR (CDCl$_3$) δ 8.1 (s, 4H), 6.7 (S, 4H), 5.1-5.3 (m, 1H), 3.9 (s, 3H), 3.1-3.9 (m, 66H), 0.6-1.8 (m, 110H). .

Example 8

Preparation of 2,2-Di(decanoyloxymethyl)propionic Acid

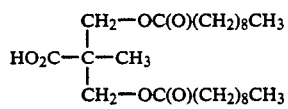

n-Decanoyl chloride (23.6 mL) was combined with 5.0 grams of 2,2-bis(hydroxymethyl)propionic acid and 100 mL of chloroform (filtered through activity I basic alumina). Triethylamine (17.1 mL) and 4-dimethylaminopyridine (2.28 grams) were then added and the resulting mixture was heated at reflux under nitrogen for 16 hours. The reaction was then cooled to room temperature and quenched with 200 mL of water. The solution was cooled to 0° C. and acidified to pH 3 with concentrated aqueous hydrochloric acid. The solution was extracted three times with methylene chloride and the combined methylene chloride layers were washed once with 1% aqueous hydrochloric acid and once with saturated aqueous sodium chloride. The organic layer was then dried over anhydrous magnesium sulfate, filtered and the solvents removed in vacuo to yield 26.01 grams of a mixture of a yellow oil and solid. The mixture was chromatographed on silica gel eluting with hexane/ethyl acetate/acetic acid (95:4:1) to yield 20.6 grams of the desired product as a light yellow oil.

Example 9

Preparation of 2,2Di(decanoyloxymethyl)propionyl Chloride

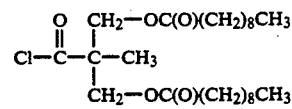

To a flask equipped with a magnetic stirrer and drying tube was added 20.6 grams of 2,2-di(decanoyloxymethyl)propionic acid from Example 8 and 200 mL of anhydrous methylene chloride and then 10.2 mL of oxalyl chloride. The resulting mixture was stirred at room temperature for 16 hours and then the solvent was removed in vacuo to yield 22.15 grams of the desired acid chloride as a yellow oil.

Example 10

Preparation of α-(4-Benzyloxyphenyl)-ω-[2,2-di(decanoyloxymethyl)-propionyloxy]poly(oxybutylene)

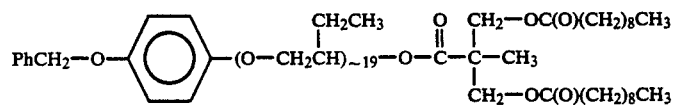

2,2-Di(decanoyloxymethyl)propionyl chloride (11.02 grams) from Example 9 was combined with 37.85 grams of α-(4-benzyloxyphenyl)-ω-hydroxypoly(oxybutylene) containing an average of 19 Oxybutylene units (prepared essentially as described in Example 1) and 180 mL of anhydrous toluene. Triethylamine (3.5 mL) and 4-dimethylaminopyridine (1.46 grams) were then added and the resulting mixture was heated at reflux under nitrogen for 16 hours. The reaction was then cooled to room temperature and diluted with 350 mL of diethyl ether. The organic layer was washed twice with 1% aqueous hydrochloric acid, twice with saturated aqueous sodium bicarbonate and once With saturated aqueous sodium bicarbonate and once with saturated aqueous sodium chloride. The organic layer was then dried over anhydrous magnesium sulfate, filtered and the solvents removed in vacuo to yield 47.12 grams of the desired ester as a brown oil.

Example 11

Preparation of α-(4-Hydroxyphenyl)-ω-[2,2di(decanoyloxymethyl)-propionyloxy]poly(oxybutylene)

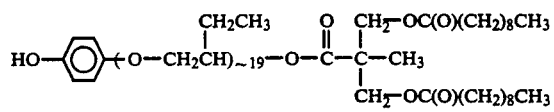

A solution of the ester from Example 10 (47.12 grams) in 100 mL of ethyl acetate and 100 mL of acetic acid containing 5.18 grams of 10% palladium on charcoal was hydrogenolyzed at 35-40 psi for 16 hours on a Parr low-pressure hydrogenator. Filtration of the catalyst and removal of solvent in vacuo followed by azeotropic removal of residual acetic acid with toluene under vacuum yielded 43.57 grams of a dark yellow oil.

The oil was chromatographed on silica gel, eluting with hexane/ethyl acetate/ethanol (80:18:2) to yield 8.54 grams of the desired product as a yellow oil. IR (neat) 1739 cm$^{-1}$; $^1$H NMR (CDCl$_3$) δ 6.7 (s, 4H), 4.8–4.9 (m, 1H), 4.2 (s, 4H), 3.0–3.8 (m, 57H), 2.25 (t, 4H), 0.6–1.7 (m, 132H).

Example 12

Single-Cylinder Engine Test

The test compounds were blended in gasoline and their deposit reducing capacity determined in an ASTM/CFR single-cylinder engine test. A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

Single-Cylinder Engine Test Results

| Sample[1] | Intake Valve Deposit Weight (in milligrams) | | |
|---|---|---|---|
| | Run 1 | Run 2 | Average |
| Base Fuel | 270.3 | 280.4 | 275.4 |
| Example 4 | 92.0 | 81.0 | 86.5 |
| Example 7 | 13.1 | 17.7 | 15.4 |
| Example 11 | 39.5 | 34.9 | 37.2 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the poly(oxyalkylene) hydroxyaromatic ethers of the present invention (Examples 4, 7, 11) compared to the base fuel.

What is claimed is:

1. A compound of the formula:

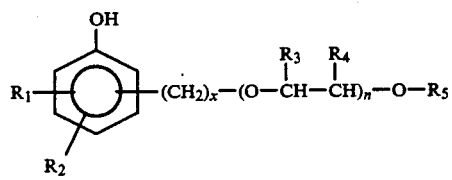

or a fuel-soluble salt thereof; wherein n is an integer from 5 to 100; x is an integer from 0 to 10;

R$_1$ and R$_2$ are each independently hydrogen, hydroxy, lower alkyl having 1 to 6 carbon atoms, or lower alkoxy having 1 to 6 carbon atoms;

R$_3$ and R$_4$ are each independently hydrogen or lower alkyl having 1 to 6 carbon atoms; and R$_5$ is acyl group of the formula:

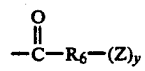

wherein y is 1, 2 or 3;

R$_6$ is a divalent hydrocarbyl radical, when y is 1, a trivalent hydrocarbyl radical, when y is 2, or tetravalent hydrocarbyl radical, when y is 3, said hydrocarbyl radicals having 1 to about 20 carbon atoms; and each Z is independently selected from the group consisting of:

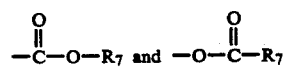

wherein each R$_7$ is independently alkyl having 1 to 30 carbon atoms, phenyl, aralkyl having 7 to 36 carbon atoms or alkaryl having 7 to 36 carbon atoms.

2. The compound according to claim 1, wherein n is an integer ranging from 5 to 50.

3. The compound according to claim 2, wherein n is an integer ranging from 10 to 30.

4. The compound according to claim 2, wherein y is 1 or 2.

5. The compound according to claim 4, wherein R$_1$ is hydrogen, hydroxy, or lower alkyl having 1 to 4 carbon atoms; and R$_2$ is hydrogen.

6. The compound according to claim 5, wherein R$_5$ is an acyl group having the formula:

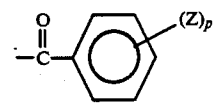

wherein p is 1 or 2; or

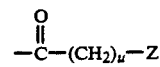

wherein u is an integer from 1 to 10; or

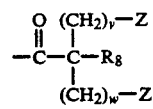

wherein R$_8$ is hydrogen or lower alkyl having 1 to about 6 carbon atoms; v is an integer from 1 to 6; and w is an integer from 1 to 6.

7. The compound according to claim 6, wherein one of R$_3$ and R$_4$ is lower alkyl having 1 to 3 carbon atoms and the other is hydrogen.

8. The compound according to claim 7, wherein x is 0, 1 or 2.

9. The compound according to claim 8, wherein one of R$_3$ and R$_4$ is methyl or ethyl and the other is hydrogen.

10. The compound according to claim 9, wherein R$_5$ is an acyl group having the formula:

wherein $R_9$ is alkyl having 1 to about 10 carbon atoms.

11. The compound according to claim 10, wherein $R_1$ is hydrogen, $R_9$ is alkyl having 1 to 6 carbon atoms, and x is 0.

12. The compound according to claim 9, wherein $R_5$ is an acyl group having the formula:

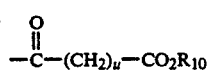

wherein $R_{10}$ is alkyl having 1 to about 10 carbon atoms and u is an integer from 1 to 10.

13. The compound according to claim 9, wherein $R_5$ is an acyl group having the formula:

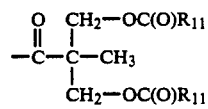

wherein $R_{11}$ is alkyl having 1 to about 10 carbon atoms.

14. A fuel composition comprising a major amount of hydrocarbons boiling in the gasoline or diesel range and an effective detergent amount of a compound of the formula:

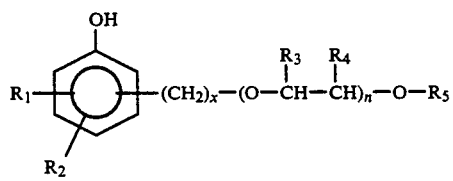

or a fuel-soluble salt thereof; wherein n is an integer from 5 to 100; x is an integer from 0 to 10;

$R_1$ and $R_2$ are each independently hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms; and $R_5$ is acyl group of the formula:

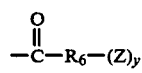

wherein y is 1, 2 or 3;

$R_6$ is a divalent hydrocarbyl radical, when y is 1, a trivalent hydrocarbyl radical, when y is 2, or tetravalent hydrocarbyl group, when y is 3, said hydrocarbyl radicals having 1 to about 20 carbon atoms; and each Z is independently selected from the group consisting of:

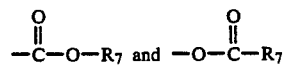

wherein each $R_7$ is independently alkyl having 1 to 30 carbon atoms, phenyl, aralkyl having 7 to 36 carbon atoms or alkaryl having 7 to 36 carbon atoms.

15. The fuel composition according to claim 14, wherein said composition contains about 50 to about 2500 parts per million by weight of said compound.

16. The fuel composition according to claim 14, wherein n is 5 to 50; x is 0, 1 or 2; $R_1$ is hydrogen, hydroxy, or lower alkyl having 1 to 4 carbon atoms; $R_2$ is hydrogen; one of $R_3$ and $R_4$ is hydrogen and the other is methyl or ethyl; and $R_5$ is an acyl group having the formula:

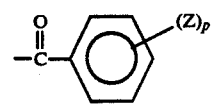

wherein p is 1 or 2; or

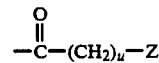

wherein u is an integer from 1 to 10; or

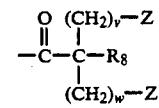

wherein $R_8$ is hydrogen or lower alkyl having 1 to about 6 carbon atoms; v is an integer from 1 to 6; and w is an integer from 1 to 6.

17. The fuel composition according to claim 16, wherein $R_5$ is an acyl group having the formula:

wherein $R_9$ is alkyl having 1 to about 10 carbon atoms.

18. The fuel composition according to claim 16, wherein $R_5$ is an acyl group having the formula:

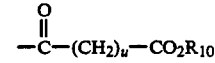

wherein $R_{10}$ is an alkyl having 1 to 10 carbon atoms and u is an integer from 1 to 10.

19. The fuel composition according to claim 16, wherein $R_5$ is an acyl group having the formula:

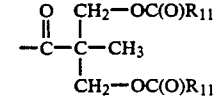

wherein $R_{11}$ is alkyl having 1 to about 10 carbon atoms.

20. A fuel concentrate comprising an inert stable oleophilic organic solvent boiling in the range of from about 150° F. to 400° F. and from about 10 to about 70 weight percent of a compound of the formula:

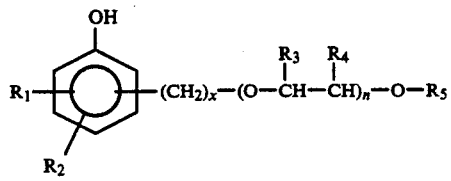

or a fuel-soluble salt thereof; wherein n is an integer from 5 to 100; x is an integer from 0 to 10;

$R_1$ and $R_2$ are each independently hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms; and $R_5$ is acyl group of the formula:

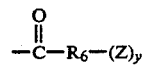

wherein y is 1, 2 or 3;

$R_6$ is a divalent hydrocarbyl radical, when y is 1, a trivalent hydrocarbyl radical, when y is 2, or tetravalent hydrocarbyl group, when y is 3, said hydrocarbyl radicals having 1 to about 20 carbon atoms; and each Z is independently selected from the group consisting of:

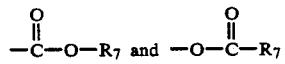

wherein each $R_7$ is independently alkyl having 1 to 30 carbon atoms, phenyl, aralkyl having 7 to 36 carbon atoms or alkaryl having 7 to 36 carbon atoms.

21. The fuel concentrate according to claim 20, wherein n is 5 to 50; x is 0, 1 or 2; $R_1$ is hydrogen, hydroxy, or lower alkyl having 1 to 4 carbon atoms; $R_2$ is hydrogen; one of $R_3$ and $R_4$ is hydrogen and the other is methyl or ethyl; and $R_5$ is an acyl group having the formula:

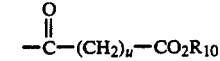

wherein p is 1 or 2; or $$-\overset{O}{\underset{\|}{C}}-(CH_2)_u-Z$$

wherein u is an integer from 1 to 10; or

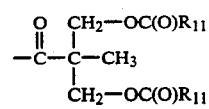

wherein $R_8$ is hydrogen or lower alkyl having 1 to about 6 carbon atoms; v is an integer from 1 to 6; and w is an integer from 1 to 6.

22. The fuel concentrate according to claim 21, wherein $R_5$ is an acyl group having the formula:

wherein $R_9$ is alkyl having 1 to about 10 carbon atoms.

23. The fuel concentrate according to claim 21, wherein $R_5$ is an acyl group having the formula:

$$-\overset{O}{\underset{\|}{C}}-(CH_2)_u-CO_2R_{10}$$

wherein $R_{10}$ is alkyl having 1 to about 10 carbon atoms and u is an integer from 1 to 10.

24. The fuel concentrate according to claim 21, wherein $R_5$ is an acyl group having the formula:

$$-\overset{O}{\underset{\|}{C}}-\underset{\underset{CH_2-OC(O)R_{11}}{|}}{\overset{\overset{CH_2-OC(O)R_{11}}{|}}{C}}-CH_3$$

wherein $R_{11}$ is alkyl having 1 to about 10 carbon atoms.

* * * * *